(12) United States Patent
DeLuca et al.

(10) Patent No.: US 7,241,900 B2
(45) Date of Patent: Jul. 10, 2007

(54) SYNTHESIS OF INDOLE THIAZOLE COMPOUNDS AS LIGANDS FOR THE AH RECEPTOR

(75) Inventors: Hector F. DeLuca, Deerfield, WI (US); Pawel K. Grzywacz, Madison, WI (US); Rafal R. Sicinski, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 41 days.

(21) Appl. No.: 11/286,537

(22) Filed: Nov. 23, 2005

(65) Prior Publication Data

US 2006/0079692 A1    Apr. 13, 2006

Related U.S. Application Data

(63) Continuation of application No. 10/364,253, filed on Feb. 11, 2003, now Pat. No. 7,002,019, which is a continuation of application No. 10/074,102, filed on Feb. 12, 2002, now Pat. No. 6,916,834.

(60) Provisional application No. 60/356,585, filed on Feb. 12, 2002.

(51) Int. Cl.
| | |
|---|---|
| C07D 277/04 | (2006.01) |
| C07D 277/08 | (2006.01) |
| C07D 263/04 | (2006.01) |
| C07D 263/08 | (2006.01) |
| C07D 403/06 | (2006.01) |
| C07D 413/06 | (2006.01) |

(52) U.S. Cl. .............. 548/201; 548/146; 548/200; 548/215; 548/237; 548/300.1; 548/312.1

(58) Field of Classification Search .......... 548/146, 548/201, 215, 237, 300.1, 312.1
See application file for complete search history.

(56) References Cited

U.S. PATENT DOCUMENTS

| | | | |
|---|---|---|---|
| 3,285,931 A | 11/1966 | Huisgen | |
| 5,366,685 A | 11/1994 | Prochaska et al. | |
| 6,323,228 B1 | 11/2001 | BaMaung et al. | |
| 6,743,919 B2 * | 6/2004 | Koya et al. | 546/118 |
| 6,916,834 B2 * | 7/2005 | DeLuca et al. | 514/365 |
| 7,002,019 B2 * | 2/2006 | DeLuca et al. | 548/146 |

OTHER PUBLICATIONS

Adachi J, et al., "Indirubin and indigo are potent aryl hydrocarbon receptor ligand present in human urine," J. Biol. Chem. 276:31475-31478 (2001).
Chen I, et al., "Indole-3-carbinol and diindolylmethane as aryl hydrocarbon (Ah) receptor agonists and antagonists in T47D human breast cancer cells," Biochem. Pharmacol. 51: 1069-1076 (1996).
Chen Y, et al., "Regulation of CYP1A1 by indolo[3,2-b]carbazole in murine hepatoma cells," J. Biol. Chem. 270:22548-22555 (1995).
Cheung Y, et al., "Interation with the aromatic hydrocarbon receptor, CYP1A induction, and mutagenicity of a series of diaminotoluenes—implications for their carcinogenicity," Toxicol. Appl. Pharmacol. 139:203-211 (1996).
Chunchatprasert L, et al., "A New Synthetic Route to Pyrrolo[3,2-b]carbozoles, 1H-Benzofuro[3,2-f]indoles and 1H-[1]Benzothieno[2,3-f]indoles," J. Chem. Soc. Perkin Trans. 1779-1783 (1992).
Chunchatprasert L & Shannon P, "Further Observations on and Novel Products from Acid-catalyzed Indole-Pyrrole Condensations: Formation of Pyrrole[2,3-b] carbazoles," J. Chem. Soc. Perkin Trans. pp. 1765-1772 (1994).
Dharmasena P, et al., "Antitumour Heterocycles. Part 12. The Synthesis of New Hydroxypyrrolocarbazoles and Hydroxypyridocarbaoles," J. Chem. Research 12-13 (1996).
Garrison P, et al., "Species-specific recombinant cell lines as bioassay systems for the detection of 2,3,7,8-tetrachlorodibenzo-p-dioxin-like chemicals," Fund. Appl. Toxicol. 30:194-203 (1996).
Hankinson O, "The Aryl Hydrocarbon Receptor Complex," Annu. Rev. Pharmacol. Toxicol. 35:307-340 (1995).
Heath-Pagliuso S, et al., "Activation of the Ah receptor by tryptophan and tryptophan metabolites," Biochem. 37:11508-11515 (1998).
Jellinck P, et al., "Ah Receptor Binding Properties of Indole Carbinols and Induction of Hepatic Estradiol Hydroxylation," Biochem. Pharmacol. 45:1129-1136 (1993).
Lee I, et al., "Transcriptional induction of the cytochrome P4501A1 gene by a thiazolium compound, YH439," Mol. Pharmacol. 49:980-988 (1996).
Liu R, et al. "Regulation of [Ah] gene battery enzymes and glutathione levels by 5,10-dihydroindeno[1,2,-b]indole in mouse hepatoma cell lines," Carcinogenesis 15:2347-2352 (1994).
Phillips A, et al., "Synthesis of Functionalized Oxazolines and Oxazoles with DAST and Deoxo-Fluor," Org. Lett. 2:1165-1168 (2000).
Poellinger L, "Regulation of Intracellular Dioxin (Aryl Hydrocarbon) Receptor Function by Dietary Indole Derivatives, Hormonally Active Agents," in Food Symposium 121-127 (1998).
Poellinger L, "Mechanistic aspects—the dioxin (aryl hydrocarbon) receptor," Food Addit. Contam. 17:261-266 (2000).
Poland A & Glover E, "Chlorinated dibenzo-p-dioxin: Potent inducers of δ-aminolevulinic acid synthetase and aryl hydrocarbon hydroxylase. II. A study of the structure-activity relationship," Mol. Pharmacol. 9:736-747 (1973).
Rannug A, et al. "Certain photooxidized derivatives of tryptophan bind with very high affinity to the Ah receptor and are likely to be endogenous signal substances," J. Biol. Chem. 262:15422-15427 (1987).

(Continued)

*Primary Examiner*—Golam M. M. Shameem
(74) *Attorney, Agent, or Firm*—Quarles & Brady LLP

(57) ABSTRACT

A method of synthesizing aromatic ketone compositions of formula I comprising the step of introducing a double bond into the 5 membered ring of the 4,5-dihydro-1,3-azoles moiety of formula II is disclosed. A method of synthesizing aromatic ketone compositions of formula I comprising the step of ring synthesis of the tetrahydro-1,3-azoles of formula XI is also disclosed.

2 Claims, 1 Drawing Sheet

OTHER PUBLICATIONS

Song J, et al., "A ligand for the aryl hydrocarbon receptor isolated from lung," Proc. Natl. Acad. Sci. USA 99:14694-14699 (2002).

Susilo R, et al., "Formation of Thiazolidine-4-Carboxylic Acid Represents a Main Metabolic Pathway of 5-Hydroxytryptamine in Rat Brain," J. Neurochem. 52:1793-1800 (1989).

Schaldach, C, et al., "Lipoxin A(4): A new class of ligand for the Ah receptor," Biochemistry 38:7594-7600 (1999).

Sinal C & Bend J, "Aryl hydrocarbon receptor-dependent induction of cyp 1a1 by bilirubin in mouse hepatoma hepa 1c1c7 cells," Mol. Pharmacol. 52:590-599 (1997).

Stephensen P, et al. "N-methoxyindole-3-carbinol is a more efficient inducer of cytochrome P-450 1A1 in cultured cells than indol-3-carbinol", Nutr. Cancer 36:112-121 (2000).

Vasiliou V, et al., "Response of [Ah] battery genes to compounds that protect against menadione toxicity," Biochem. Pharmacol. 50:1885-1891 (1995).

Washburn B, et al., "Brevetoxin-6 (pbtx-6), a nonaromatic marine neurotoxin, is a ligand of the aryl hydrocarbon receptor," Arc. Biochem. Biophy. 343:149-156 (1997).

Whitlock J, et al., "Genetic and molecular aspects of 2,3,7,8-tetrachlorodibenzo-p-dioxin action," Ann. Rev. Pharmacol. Toxicol. 30:251-277 (1990).

* cited by examiner

SYNTHESIS OF INDOLE THIAZOLE COMPOUNDS AS LIGANDS FOR THE AH RECEPTOR

CROSS-REFERENCE TO RELATED APPLICATIONS

This application is a continuation of U.S. Ser. No. 10/364,253, filed Feb. 11, 2003 now U.S. Pat. No. 7,002,019, which claims priority from provisional patent application Ser. No. 60/356,585, filed Feb. 12, 2002, and U.S. Ser. No. 10/074,102, filed Feb. 12, 2002 now U.S. Pat. No. 6,916,834, all incorporated by reference herein.

STATEMENT REGARDING FEDERALLY SPONSORED RESEARCH OR DEVELOPMENT

BACKGROUND OF THE INVENTION

The Aryl Hydrocarbon Receptor. The aryl hydrocarbon receptor (AhR) is a ligand inducible transcription factor mediating a broad spectrum of biological processes upon binding to its ligand. Besides induction of enzymes in the cytochrome P450 family, the receptor appears involved with cell proliferation, tumor promotion, immune suppression, vitamin A depletion, and developmental and reproductive abnormalities (Fletcher, et al., Toxicol. Sci. 62(1):166–175, 2001; Safe, Toxicol. Let. 120:1–7, 2001; Gu, et al., Ann. Rev. Pharmacol. Toxicol. 40:519–561, 2000; Poellinger, Food Add. Contam. 17(4):261–266, 2000; Schmidt and Bradfield, Ann. Rev. Cell Dev. Biol. 12:55–89, 1996; Whitlock, et al., Drug Metabol. Rev. 29:1107–1127, 1997). The liganded receptor also causes cell cycle arrest, apoptosis, adipose differentiation, and anti-estrogen effects (Bonnesen, et al., Cancer Res. 61(16):6120–6130, 2001; Elferink, et al., Mol. Pharmacol. 59(4):664–673, 2001; Shimba, et al., J. Cell Sci. 114(15):2809–2817, 2001; Shimba, et al., Biochem. Biophy. Res. Com. 249(1):131–137, 1998; Safe, supra, 2001; McDougal, et al., Cancer Res. 61(10):3902–3907, 2001; McDougal, et al., Cancer Lett. 151:169–179 2000; Elizondo, et al., Mol. Pharmacol. 57(5):1056–1063, 2000; Puga, et al., J. Biol. Chem. 275(4):2943–2950, 2000; Alexander, et al., J. Cell Sci. 111(Part 22):3311–3322, 1998). The presence of the receptor was proposed and evidenced in 1970's (Poland, et al., J. Biol. Chem. 251:4936–4946, 1976). The coding sequence for the receptor was cloned in 1990's and revealed that the AhR is a member of an emerging basic Helix-Loop-Helix/Pas-Arnt-Sim (bHLH/PAS) transcription factor super family (Burbach, et al., Proc. Natl. Acad. Sci. USA 89:8185–8189, 1992).

The bHLH/PAS Super Family of Transcription Factors. The bHLH/PAS super family includes Drosophila Per, Arnt (Ah receptor nuclear translocator, the dimerization partner of AhR and others), SIM1, SIM2, TRH, ARNT-2, the hypoxia inducible factor-1 (HIF-1α), SRC-1, TIF2, RAC3, MOPs 2–5 (Gu, et al., supra, 2000; Hogenesch, et al., J. Biol. Chem. 272:8581–8593, 1997; Wilk, et al., Genes Dev. 10:93–102, 1996), and endothelial PAS domain protein (EPAS-1) (Tian, et al., Genes Dev. 11:72–82, 1997). These bHLH proteins contain the 300 amino acid PAS domain, composed of two 50 amino acid degenerate direct repeats (Burbach, et al., supra, 1992; Dolwick, et al., Mol. Pharmacol. 44:911–917, 1993; Dolwick, et al., Proc. Natl. Acad. Sci. USA 90:8566–70, 1993). The basic region is important for DNA binding, and the HLH and PAS domains are involved in dimerization, and for AhR, in ligand binding (Swanson and Bradfield, Pharmacogenetics 3:213–230, 1993). The transactivation domains of the AhR and ARNT map to their carboxyl termini (Jain, et al., J. Biol. Chem. 269:31518–31524, 1994). Members of this super family are master developmental regulators and it is intriguing to speculate similar roles for AhR and ARNT. Besides with AhR, ARNT forms heterodimers also with HIF-1α, PER, SIM, MOP2 (Hogenesch, et al., supra, 1997), and EPAS-1 (Tian, et al., supra, 1997) and an ARNT-related protein is postulated to heterodimerize with TRH (Wilk, et al., supra, 1996). This promiscuity of ARNT indicates AhR-independent roles for ARNT and suggests the possibility of cross talk between AhR and the other bHLH/PAS signaling pathways.

The Homeostatic Response to Hypoxia: Role of HIF-1a/ARNT-Mediated Gene Expression. Vertebrates require molecular oxygen for vital metabolic processes. Homeostatic responses elicited by hypoxia include erythropoiesis, angiogenesis, and glycolysis. These adaptive responses serve to increase oxygen delivery or activate alternative metabolic pathways that do not require oxygen in hypoxic tissues. In response to hypoxia, HIF-1α translocate into the nucleus where they form heterodimers with ARNT (Gradin, et al., Mol. Cell. Biol. 16(10):5221–31, 1996; Schmidt and Bradfield, supra, 1996). The HIF-1α/ARNT heterodimers bind to hypoxia response elements increasing transcription of genes involved in maintaining oxygenation of tissues. The hypoxia-inducible gene products include erythropoietin (EPO), vascular endothelial growth factor (VEGF), and glycolytic enzymes (Maltepe and Simon, J. Mol. Med. 76(6):391–401, 1998).

The Mode of Action of AhR/ARNT Signaling Pathway. The cytoplasmic form of AhR is associated with 2 molecules of heat shock protein (hsp90) and some other cellular factors (Poellinger, supra, 2000; Whitlock, Ann. Rev. Pharmacol. Toxicol. 30:251–277, 1990). After ligand binding, the hsp90 and the other factors dissociate and AhR is activated. The activated AhR then translocates into the nucleus and dimerizes with its partner ARNT (Probst, et al., Mol. Pharmacol. 44:511–518, 1993). AhR/ARNT heterodimers recognize and bind the so-called xenobiotic response elements (XREs) found in promoters of AhR controlled genes to alter gene expression (Whitlock, supra, 1990). Another potential mechanism involves competition between AhR and either HIF-1α and/or EPAS-1 for dimerization with ARNT. Since AhR, HIF-1α and EPAS-1 require dimerization with ARNT to control the expressions of their target genes, activation of AhR might reduce the availability of free ARNT to such an extent that it becomes rate limiting for other signaling pathways. Decreased availability of ARNT could lead to decreased expression of vital hypoxia-regulated genes and angiogenesis blockage, for example, by inhibiting HIF-1α signaling (Gradin, et al., supra, 1996; Schmidt and Bradfield, supra, 1996).

The Known AhR Ligands. Among the first discovered human-made ligands for the AhR are the chemicals known as polycyclic aromatic hydrocarbons such as 3-methylcholanthrene and benzo[α]pyrene. A much more potent and higher affinity ligand, 2,3,7,8-tetrachlorodibenzo-p-dioxin (TCDD), was discovered (Poland and Glover, Mol. Pharmacol. 9:736–747, 1973). Another structural group of compounds, halogenated aromatic hydrocarbons, was recognized as the receptor ligands. The compounds with different structural characteristics from the groups mentioned were also found to have binding affinity to AhR. This group is represented by bilirubin (Phelan, et al., *Arc. Biochem. Biophy.* 357(1):155–163, 1998; Sinal and Bend, *Mol. Pharmacol.* 52(4):590–599, 1997), lipoxin A(4) (Schaldach, et al., *Biochem.* 38(23):7594–7600, 1999), brevetoxin-6 (Washburn, et al., *Arc. Biochem. Biophy.* 343(2):149–156, 1997), diaminotoluene (Cheung, et al., *Toxicol. Appl. Pharmacol.* 139(1):203–211, 1996), and YH439, a thiazolium compound (Lee, et al., *Mol. Pharmacol.* 49(6):980–988, 1996). Among most of the human-made AhR ligands, TCDD is one of the most potent agents for AhR and is the prototype compound used to study the mechanism of AhR action and dioxin toxicity. The term "dioxins" has been used to refer to any of the PCDDs (polychlorinated dibenzo-p-dioxins), PCDFs (polychlorinated dibenzofurans), or PCBs (polychlorinated biphenyls) that cause the same biological responses, by the same mechanism as TCDD.

The AhR Ligands with an Indole Moiety. The other recognized AhR ligands with an indole moiety are of special interest. This group consists of tryptamine, indole acetic acid (Heathpagliuso, et al., *Biochem.* 37(33):11508–11515, 1998), indole-3-carbinol and its derivatives (Stephensen, et al., *Nutr Cancer Internatl. J.* 36(1):112–121, 2000; Chen, et al., *Biochem. Pharmacol.* 51(8):1069–1076, 1996; Vasiliou, et al., *Biochem. Pharmacol.* 50(11):1885–1891, 1995; Liu, et al., *Carcinogenesis.* 15(10):2347–2352, 1994; Jellinck, et al., *Biochem. Pharmacol.* 45(5):1129–1136, 1993), and indolo[3,2-b]carbazole (ICZ) (Chen, et al., *J. Biol. Chem.* 270(38):22548–22555, 1995; Kleman, et al., *J. Biol. Chem.*, 269(7):5137–5144, 1994). Closely related to ICZ, 6-formylindolo[3,2-b]carbazole derived from tryptophan by UV oxidation has higher affinity than that of TCDD to the receptor (Rannug, et al., *Chem. Biol.* 2(12):841–845, 1995; Rannug, et al., *J. Biol. Chem.* 262:15422–15427, 1987). Some of the indole derived AhR ligands displayed their interesting properties: binding to the receptor, low toxicity, antiestrogenic and antitumorigenic. Actually, clinical studies have been launched for indole-3-carbinol as an anticarcinogenic and antitumorigenic remedy for patients with high risk of tumorigenesis (Preobrazhenskaya and Korolev, *Bioorganicheskaya Khimiya.* 26(2):97–111, 2000).

Identity of the Endogenous AhR Ligand and Physiological Functions of the Ah Receptor System Are not Resolved. Okamoto, et al. (Okamoto, et al., *Biochem. Biophys. Res. Commun.* 197:878–885, 1993) observed that exposure of adult male rats to hyperoxia (95% oxygen) caused induction of CYP1A1 in the lung and CYP1A1 and 1A2 in the liver. The induction of CYP1A1/1A2 is usually associated with the binding of AhR to its ligands. One hypothesis to explain CYP1A1/1A2 induction by hyperoxia is that an endogenous ligand(s) of the AhR is produced by hyperoxia, which activates the transcription of CYP1A1/1A2 genes (Okamoto, et al., supra, 1993). Recently two human urinary products were isolated that bind to the AhR (Adachi, et al., *J. Biol. Chem.* 276(34):31475–31478, 2001). Whether those products are endogenous ligands or not is undetermined because the identified compounds are indigo, a commonly used fabric dye, and indirubin, an isomer of indigo. Since they were isolated from urine, the question of whether they are urinary excretion products remains unanswered. Similarly, the bilirubin-related compounds (Phelan, et al., supra, 1998; Sinal and Bend, supra, 1997) and lipoxin A(4) (Schaldach, et al., supra, 1999) are certainly endogenous in nature but whether they are the true ligands for the AhR has not yet been resolved. The response and affinity for the AhR appear to be, in fact, quite low for these compounds.

The generation of AhR-deficient mice illustrates possible physiological functions of the receptor in liver, heart, ovary, and the immune system, even though it is not conclusive at this point (Benedict, et al., *Toxicol. Sci.* 56(2):382–388, 2000; Poellinger, supra, 2000; Mimura, et al., *Gene. Cell.* 2:645–654, 1997; Schmidt, et al., *Proc. Nat. Acad. Sci. USA* 93:6731–6736, 1996; Fernandez-Salguero, et al., *Science* 268:722–726, 1995). The significance of those findings is that they demonstrate a need for a functioning AhR signaling pathway in animal physiology. It is probable that endogenous AhR ligands in animal tissues are involved in carrying out this AhR signaling function.

Importance of Identifying the Endogenous AhR Ligands. Studies with human-made AhR ligands on this receptor system greatly advanced our understanding in this system. It is clear, however, that the AhR did not develop in an evolutionary sense to react to manufactured chemical agents. It is reasonable to suspect that there must be an endogenous ligand for the AhR, which should be nontoxic at tissue concentrations normally encountered in the body, rapidly cleared by metabolism, and utilized to activate the AhR only transiently in a regulatory capacity. Also, evidence shows that the different outcomes of the ligand-receptor mediated signaling processes are possible and dependent upon the nature of the ligands. A decisive factor dictating the consequences in the ligand-receptor mediated signal transducing systems is the final three dimensional conformation of the liganded receptor assumes because that conformation determines the ways the liganded receptor interacts with numerous other factors to transduce signals. Given the amino acid sequence of the receptor, the final three-dimensional structure of the liganded receptor is solely dependent on the structure of the ligand, which ultimately dictates the biological outcomes of the signaling system. To completely understand the physiological functions of the Ah receptor system and the potential therapeutic benefits this system may offer, the identification and synthesis of the AhR ligand is an absolute necessity.

BRIEF SUMMARY OF THE INVENTION

In one embodiment, the present invention is a method of synthesizing aromatic ketone compositions of formula I

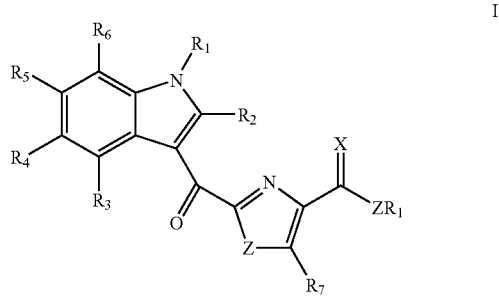

wherein:

$R_1$ may be hydrogen or can be selected from the group consisting of $(C_1–C_6)$-alkyl and $(C_3–C_7)$-cycloalkyl, and wherein the alkyl group can be substituted by $(C_3-C_7)$-cycloalkyl or can be mono- or polysubstituted by an aryl group, wherein the aryl group can be mono- or polysubstituted by halogen, $(C_1-C_6)$-alkyl, $(C_3-C_7)$-cycloalkyl, hydroxy and nitro groups; $R_1$ may be an aryl group, wherein the aryl group can be mono- or polysubstituted by halogen, $(C_1-C_6)$-alkyl, $(C_3-C_7)$-cycloalkyl, hydroxy and nitro groups; $R_1$ may further be a protecting group;

$R_2$, $R_3$, $R_4$, $R_5$, $R_6$, and $R_7$ may be the same or different and are each selected from the group consisting of hydrogen, $(C_1-C_6)$-alkyl, $(C_3-C_7)$-cycloalkyl, $(C_1-C_6)$-acyl, $(C_1-C_6)$-alkoxy, alkoxycarbonyl (COOR$_1$), halogen, benzyloxy, the nitro group, the amino group, the $(C_1-C_4)$-mono or dialkyl-substituted amino group, or an aryl group, wherein the aryl group can be mono- or polysubstituted by halogen, $(C_1-C_6)$-alkyl, $(C_3-C_7)$-cycloalkyl, hydroxy and nitro groups;

X and Z may be the same or different and are each selected from the group consisting of O, S and NH. The method comprises the step of introducing a double bond into the 5 membered ring of the 4,5-dihydro-1,3-azoles moiety of a compound of the formula II

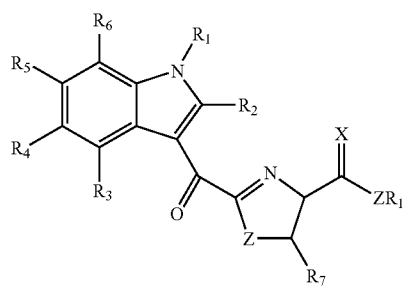

II wherein the stereochemical centers may have R or S configuration.

In a preferred embodiment, preferably with MnO$_2$ or NiO$_2$.

In one embodiment, the compound of formula II is prepared by cyclization of the derivatives of the N-substituted indole-3-glyoxylamide of formula III

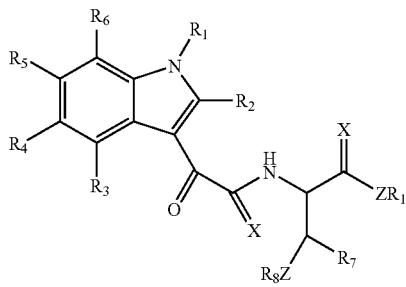

III where $R_8$ represents hydrogen or a protecting group.

In one embodiment, the compound of formula II is prepared by cyclization of derivatives of the indole-3-glyoxylates of formula IV

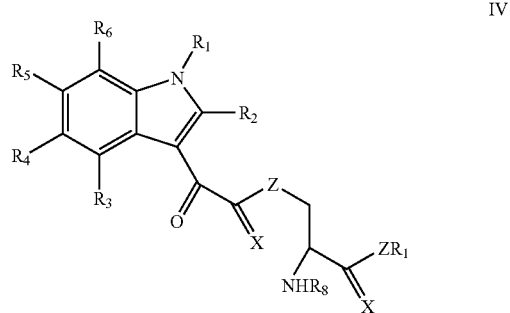

IV where Z may be O or S, and $R_8$ represents hydrogen or the protecting group.

In one embodiment, the derivatives of the N-substituted indole-3-glyoxylamide of formula III are obtained from derivatives of indole-3-glyoxylic acid of formula V, and the corresponding amines of formula VI

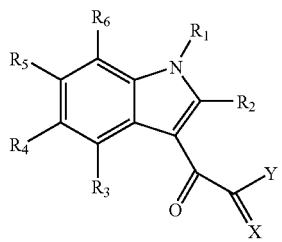

V

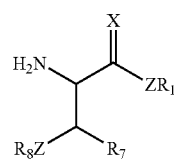

VI where Y is selected from amino group, halogen, hydroxyl, alkoxy group (OR$_1$), mercapto group (SH) or alkylthio group (SR$_1$).

In another embodiment, derivatives of formula IV are obtained from the derivatives of indole-3-glyoxylic acid of formula V, and the corresponding alcohols or thiols of formula VIII.

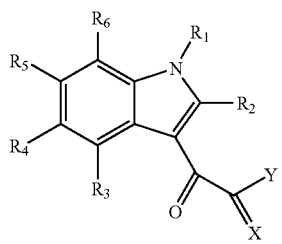

V

-continued

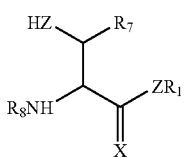
VII

In another embodiment, the present invention is a method of synthesizing aromatic ketone compositions of formula I comprising the step of introducing two double bonds into the 5 membered ring of the tetrahydro-1,3-azoles of formula XI.

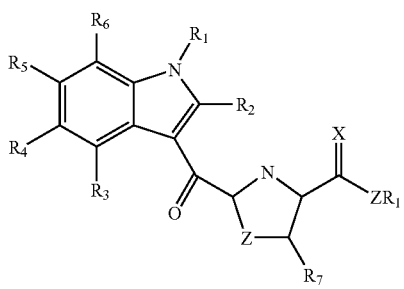
XI

In a preferred embodiment, the compound of formula XI is prepared from derivatives of the indole-3-glyoxals of formula X and the corresponding amines of formula VI.

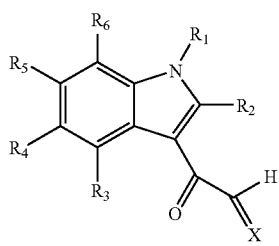
X

In another embodiment, the present invention additionally comprising the step of testing the compounds for efficacy as an AHR ligand.

In another embodiment, the present invention is a compound of the formula II

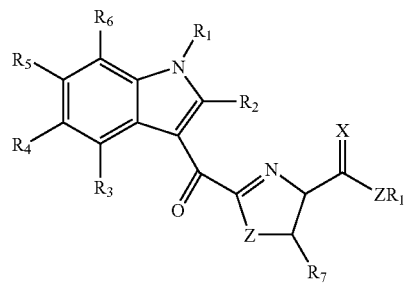
II where $R_1$, $R_2$, $R_3$, $R_4$, $R_5$, $R_6$, $R_7$, X, and Z are as defined in claim 1, and where the stereochemical centers, i.e., the carbons bearing $C(X)ZR_1$ and $R_7$ substituent may have R or S configuration.

In another embodiment, the present invention is a compound of the formula III

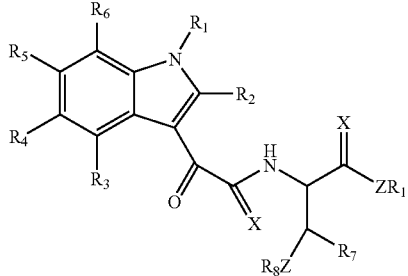
III wherein:
$R_1$, $R_2$, $R_3$, $R_4$, $R_5$, $R_6$, $R_7$, X, and Z are as defined in claim 1; $R_8$ represents hydrogen or the protecting group; the stereochemical centers, i.e., the carbons bearing $C(X)ZR_1$ and $R_7$ substituent may have R or S configuration; with the proviso that when $R_7$ and $R_8$ are hydrogens, and X is an oxygen, Z can not be oxygen.

In another embodiment, the present invention is a compound of the formula IV

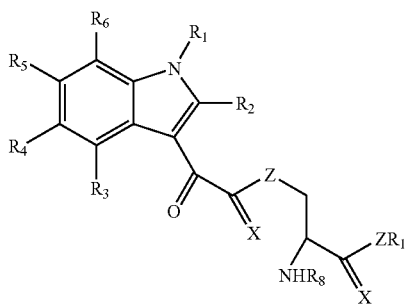
IV wherein:
$R_1$, $R_2$, $R_3$, $R_4$, $R_5$, $R_6$, X, and Z are as defined in claim 1; $R_8$ represents hydrogen or the protecting group; Z may be O or S the stereochemical center, i.e., the carbon bearing $NHR_8$ substituent may have R or S configuration.

In another embodiment, the present invention is a compound of the formula XI

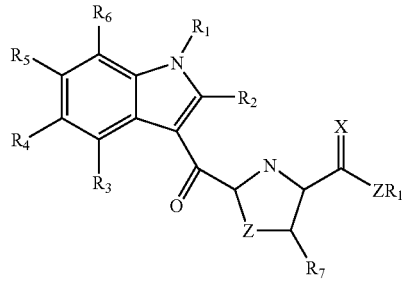
XI where $R_1$, $R_2$, $R_3$, $R_4$, $R_5$, $R_6$, $R_7$, X, and Z are as defined in claim 1, and where all the stereochemical centers of the tetrahydro-1,3-azole fragment may have R or S configuration.

DETAILED DESCRIPTION OF THE INVENTION

Figure 1:
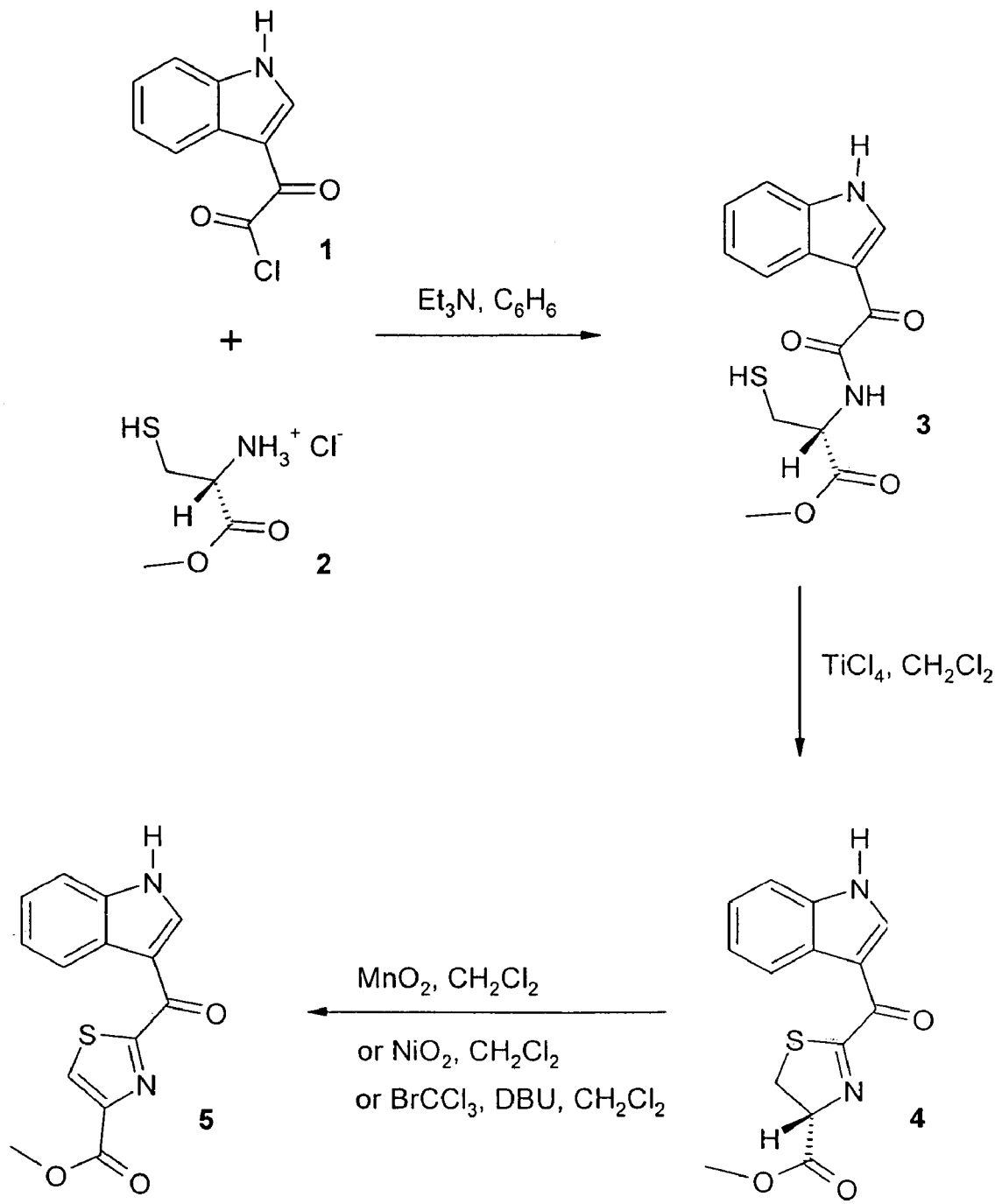
FIG. 1 is a scheme describing a preferred embodiment of the present invention.

The present invention relates to a process for preparing certain aromatic ketones possessing two heterocyclic moieties attached to a carbonyl group. One moiety comprises an indole (or substituted indole) fragment that is attached to the carbonyl group by carbon 3 of the indole. The other heterocyclic moiety comprises a five-membered 1,3-azole ring of imidazole, oxazole or thiazole, attached to the carbonyl group by the carbon 2 and possessing carboxyl group (free or derivatized) as substituent at carbon 4.

Compounds of the present invention are envisioned to have efficacy as AhR ligands. Characterization and function of the AhR ligand is described in U.S. provisional patent application 60/268,809 and U.S. patent application Ser. No. 10/074,102, filed Feb. 12, 2002. Both of these applications are incorporated by reference as if set forth in their entirety.

Thus, the present invention provides a process for preparing compounds represented by the general formula I:

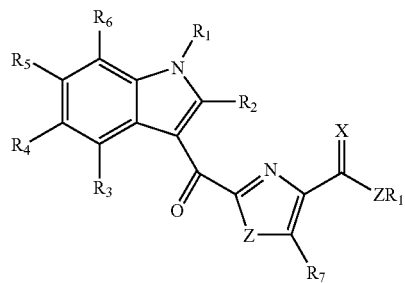

I wherein:

$R_1$ may be hydrogen or can be selected from the group consisting of $(C_1-C_6)$-alkyl and $(C_3-C_7)$-cycloalkyl, wherein the alkyl group can be substituted by $(C_3-C_7)$-cycloalkyl, or can be mono- or polysubstituted by the aryl group, wherein the aryl group can be mono- or polysubstituted by halogen, $(C_1-C_6)$-alkyl, $(C_3-C_7)$-cycloalkyl, hydroxy and nitro groups, $R_1$ may be an aryl group, wherein the aryl group can be mono- or polysubstituted by halogen, $(C_1-C_6)$-alkyl, $(C_3-C_7)$-cycloalkyl, hydroxy and nitro groups, $R_1$ may be a protecting group, $R_2$, $R_3$, $R_4$, $R_5$, $R_6$, and $R_7$ may be the same or different and are selected from the group consisting of hydrogen, $(C_1-C_6)$-alkyl, $(C_3-C_7)$-cycloalkyl, $(C_1-C_6)$-acyl, $(C_1-C_6)$-alkoxy, alkoxycarbonyl (COOR$_1$), halogen, benzyloxy, the nitro group, the amino group, the $(C_1-C_4)$-mono and dialkyl-substituted amino group or an aryl group, wherein the aryl group may be mono- or poly-substituted by halogen, $(C_1-C_6)$-alkyl, $(C_3-C_7)$-cycloalkyl, hydroxy and nitro groups, and X and Z may be the same or different and are selected from the group consisting of O, S and NH.

In the method of the present invention, the compounds of formula I are preferably prepared from indole derivatives of the general formula II:

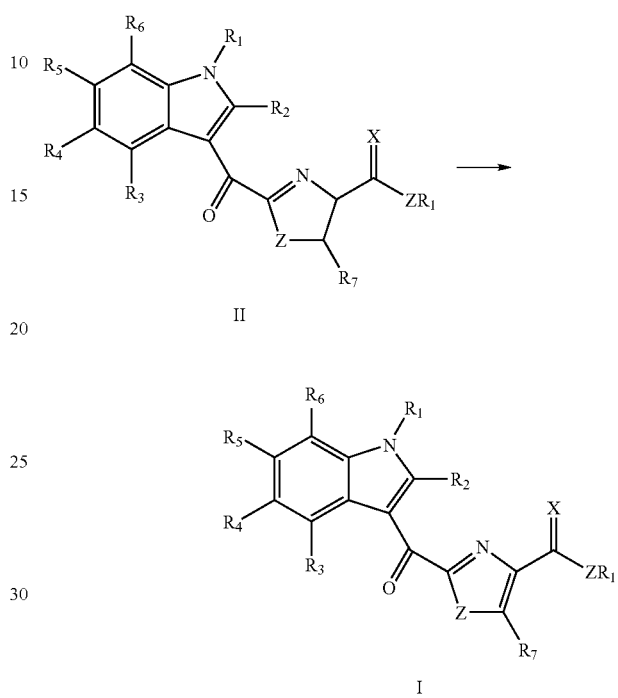

II

I where the stereochemical centers, i.e., the carbons bearing $C(X)ZR_1$ and $R_7$ substituent may have R or S configuration.

Such introduction of an additional double bond to the five membered ring of the 4,5-dihydro-1,3-azoles II can be a one-step dehydrogenation or can comprise two steps. For example, allylic bromination/dehydrobromination procedures are suitable. In the first case, suitable reagents causing dehydrogenation of dihydro derivatives of nitrogen-, oxygen-, and sulfur-containing heterocycles are $MnO_2$ (North and Pattenden, *Tetrahedron* 46:8267, 1990) and $NiO_2$ (Minster, et al., *J. Org. Chem.* 43:1624, 1978; Evans, et al., *J. Org. Chem.* 44:497, 1979). However, other reagents can be satisfactorily employed for such transformation, including sulfur, oxygen, potassium ferricyanide, mercuric acetate, hydrogen peroxide, potassium dichromate, cupric sulfate, ferric chloride, phenanthrene-9,10-dione and other quinones. Examples of the methods which can be used for two-step conversion of II to the fully aromatic compounds I involve a treatment with $BrCCl_3$ and DBU (Williams, et al., *Tetrahedron Lett.* 38:331, 1997; Freeman and Pattenden, *Tetrahedron Lett.* 39:3251, 1998), NBS/hv (Meyers and Tavares, *Tetrahedron Lett.* 35:2481, 1994) and phenylselenenylation/elimination (Nakamura, et al., *Tetrahedron Lett.* 36:5059, 1995).

Compounds of the general formula II, in turn, can be prepared by cyclization of the derivatives of N-substituted indole-3-glyoxylamides of the general formula III (where Z is NH, O or S) or derivatives of indole-3-glyoxylates of the general formula IV (where Z is O or S):

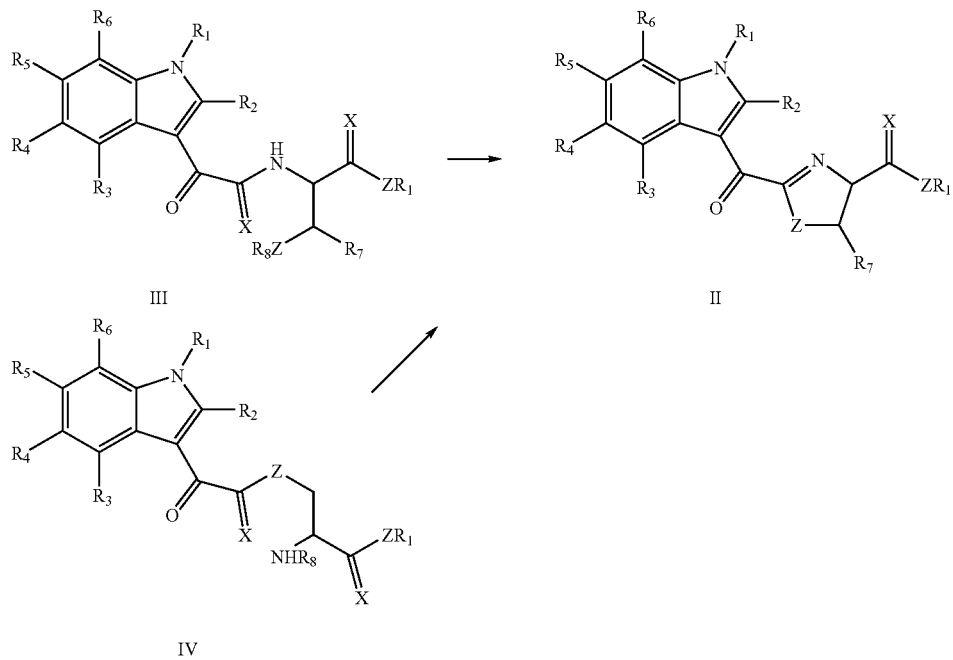

where:

$R_8$ represents hydrogen or a protecting group.

It can be expected that acidic conditions, for example anhydrous hydrochloric acid (McGowan, et al., *J. Am. Chem. Soc.* 99:8078, 1977) or strong Lewis acid such as TiCl$_4$ (Walker and Heathcock, *J. Org. Chem.* 57:5566, 1992) would be desirable for such cyclizations because they could enhance a reactivity of C=X group for nucleophilic attack of amino, hydroxy or thiol group. Presence of strong acids in the reaction medium could also facilitate a subsequent dehydration process (when X=O), evolution of H$_2$S (when X=S), or evolution of NH$_3$ (when X=NH) from the intermediates. The examples of other reagents which can be useful for such transformations are H$_2$SO$_4$, P$_2$O$_5$, PCl$_5$, SOCl$_2$ and Al$_2$O$_3$. Suitable solvents for such dehydrative cyclizations can be chlorinated hydrocarbons such as chloroform or methylene chloride. It should be added that, depending on the conditions of the reaction, such cyclization can be successfully accomplished without prior removal of S—, O— or N-protecting groups.

The derivatives of N-substituted indole-3-glyoxylamides of the general formula III (where Z is NH, O or S) can be obtained from the derivatives of indole-3-glyoxylic acid V and the corresponding amines VI:

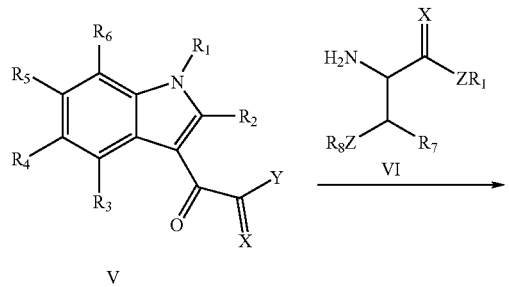

-continued

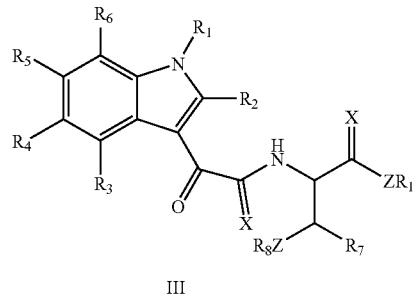

where:

Y is selected from amino group, halogen, hydroxyl, alkoxy group (OR$_1$), mercapto group (SH) or alkylthio group (SR$_1$).

For transformation of V to III conditions usually used for the synthesis of amides would be appropriate, such as, neutral solvent (for example benzene) and a presence of pyridine or tertiary amine (triethylamine, etc) as a catalyst. The compounds VI can be free amines or the corresponding amine salts (hydrochlorides, etc). It should be emphasized that, depending on the nature of reagents and reaction conditions, the reaction between V and VI can directly provide cyclised compounds of the general formula II. Such situation can take place, for example, with imino ethers V (where X=NH and Y=OR$_1$, see North and Pattenden, *Tetrahedron* 46:8267, 1990).

Derivatives of indole-3-glyoxylates of the general formula IV (where Z is O or S) can be obtained from the derivatives of indole-3-glyoxylic acid V and the corresponding alcohols (thiols) VII:

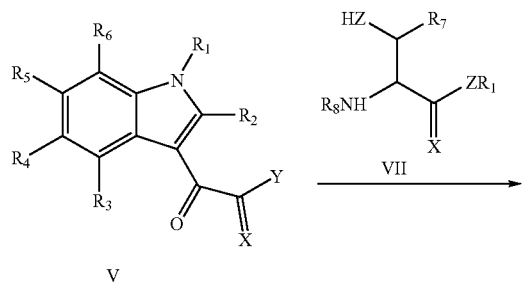

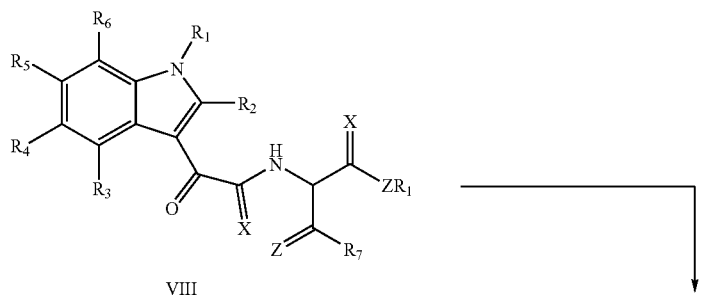

Conditions known by those of skill in the art as suitable for ester formation should be used.

The derivatives of indole-3-glyoxylic acid V are the known compounds or they can be obtained by modification of the known methods. Thus, for example, derivatives of 3-indoleglyoxylyl chlorides V (X=O, Y=Cl) can be efficiently obtained by acylation of the corresponding indoles with oxalyl chloride (Da Settimo, et al., *Eur. J. Med. Chem.* 23:21, 1988; *J. Med. Chem.* 39:5083, 1996). It should be emphasized that, depending on the nature of reagents and reaction conditions, the reaction between V and VII can directly provide cyclised compounds of the general formula II.

Alternatively, the compounds of formula I can be prepared by cyclization of the derivatives of N-substituted indole-3-glyoxylamides of the general formula VIII or condensation of the derivatives of indole-3-glyoxylamides of the general formula IX with the carbonyl compounds X:

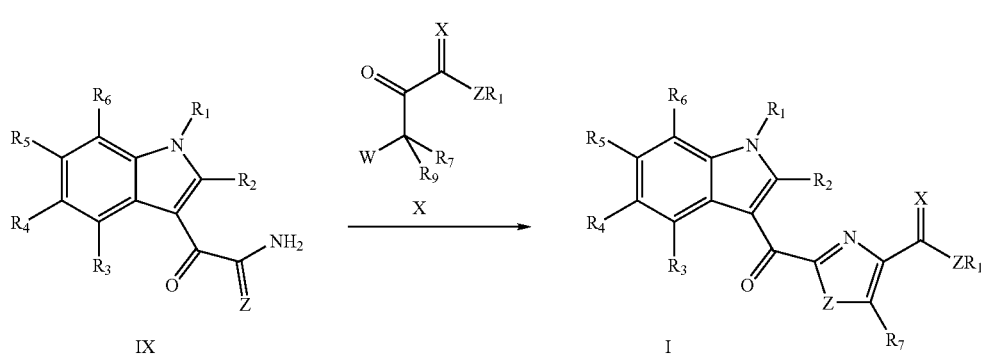

where:

W can be halogen, hydroxyl or taken together with $R_9$ is a diazo ($=N_2$) group, and $R_9$ is hydrogen or taken together with W is diazo ($=N_2$) group.

The cyclization process of VIII leading to compounds I is usually an acid-catalyzed reaction. Usually the condensation of IX and X requires their heating in an inert solvent, sometimes a presence of Lewis acids can be also advantageous.

Alternatively, the preparation of the compounds of the general formula I can be achieved by the ring synthesis of the tetrahydro-1,3-azoles of the general formula XI, i.e., the formation of N,N-, N,O- or N,S-analogues of cyclic acetals of the derivatives of the indole-3-glyoxals X and their subsequent dehydrogenation:

trifluoroacetyl, etc. The "amino-protecting groups" are, for example, alkyl carbamates such as allyl carbamate (Alloc), t-butyl carbamate (BOC) and benzyl carbamate (Cbz) or amines can be protected as the corresponding amides such as chloroacetamide, trifluoroacetamide (TFA), etc.

"Alkyl" signifies a straight-chain or branched hydrocarbon radical of 1 to 6 carbons in all its isomeric forms, such as methyl, ethyl, propyl, isopropyl, butyl, isobutyl, pentyl, etc., and the term "cycloalkyl" is understood as meaning radicals such as, for example; cyclopropyl, cyclobutyl, cycloheksyl, etc. The designation "alkoxy group" represents radicals such as, for example, methoxy, ethoxy, butoxy, etc. The term "acyl" means an alkanoyl group of 1 to 6 carbons in all its isomeric forms, such as formyl, acetyl, propionyl, etc. or an aroyl group, such as benzoyl, nitrobenzoyl or halobenzoyl, or a dicarboxylic acyl group such as oxalyl,

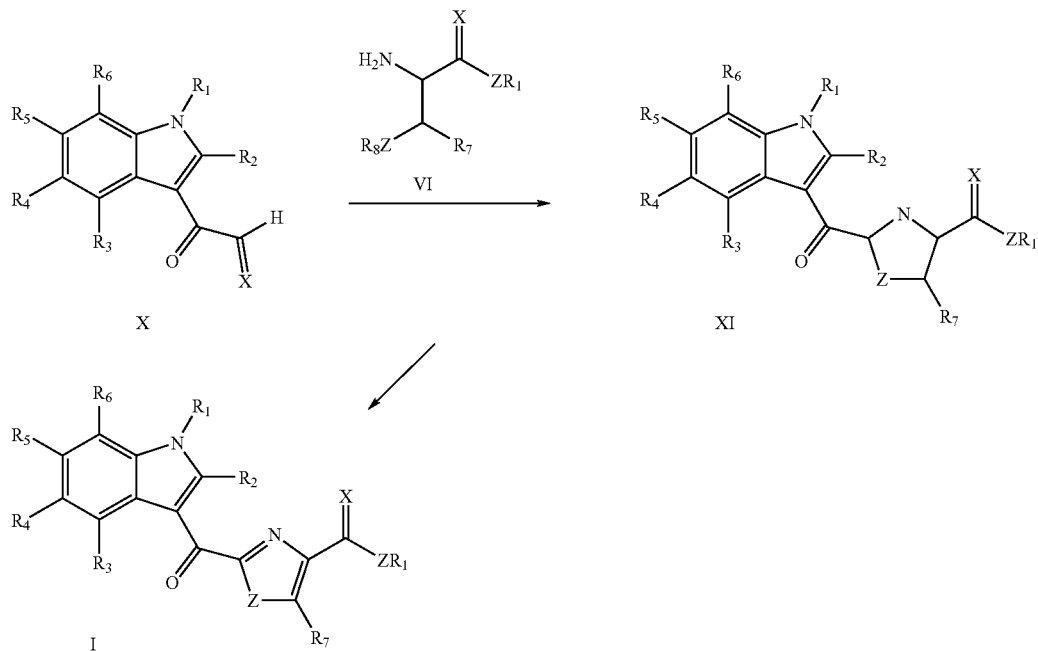

Such condensation process of X and VI usually requires heating of both compounds in an inert solvent. For dehydrogenation of the tetrahydro-1,3-azoles XI similar reagents and conditions can be applied as in the case of conversion of 4,5-dihydro-1,3-azoles II to the fully aromatic compounds I (see above).

In this specification and the claims, the term "protecting group" refers to any group commonly used for the protection of hydroxyl, thiol and amino functions during subsequent reactions. Such protecting groups are discussed by T. W. Greene and P. G. M. Wuts in chapters 2, 6 and 7, respectively, of "Protective Groups in Organic Synthesis", John Wiley and Sons, Inc., New York, 1999, incorporated herein by reference in their entirety. The "hydroxyl-protecting groups" are acyl or alkylsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. The "thiol-protecting groups" are alkyl or arylalkyl groups such as t-butyl, benzyl, adamantyl, cyanoethyl, etc. or acyl groups such as acetyl, benzoyl, malonyl, succinoyl, glutaroyl, or adipoyl. The term "aryl" signifies a phenyl-, or an alkyl-, halo-, nitro- or hydroxy-substituted phenyl group. The designation "halogen" represents fluorine, chlorine, bromine or iodine.

This invention is described by the following illustrative examples. In these examples specific products identified by Arabic numerals (e.g. 1, 2, 3, etc) refer to the specific structures so identified in the Scheme I in FIG. 1.

EXAMPLES

The endogenous ligand for the aryl hydrocarbon receptor (AHR), 2-(1'H-indole-3'-carbonyl)-thiazole-4-carboxylic acid methyl ester (ITE, 5, Scheme 1), has been isolated in very small quantities (ca. 20 μg) and identified through extensive spectral studies. Given the biological importance of the ligand, its chemical synthesis was obviously necessary for confirmation of the structural assignment and preparation of larger amounts of compound needed for studies of its physiological activity. Since the molecule of this aromatic ketone consists of two heterocyclic fragments, indole and 4-carbomethoxythiazole attached to the carbonyl group, we sought possible synthetic routes involving intermediate indole glyoxylamides.

Thus, we decided to prepare the desired compound (5) from glyoxylamide (3). The latter compound was easily obtained by acylation of the L-cysteine methyl ester (2) with indoleglyoxylyl chloride (1) carried out in the benzene solution containing triethylamine (Da Settimo, et al., *J. Med. Chem.* 39:5083, 1996). Next, we performed cyclization of the glyoxylamide (3) by employing reaction conditions used by Mann, et al. (Martin, et al., *J. Chem. Soc. Perkin Trans.* 1:2455, 1999) in their preparation of analogs of curacin A, i.e. treatment with $TiCl_4$ in dichloromethane. This methodology allowed us to isolate the desired thiazoline ester (4) in 25% yield. Finally, three different methods of oxidation of thiazoline (4) were examined. Thus, treatment of 4 with $MnO_2$ or $NiO_2$ in dichloromethane provided the indolecarbonyl-thiazole (5) in satisfactory yields (88 and 75%, respectively). A mild method of dehydrogenation described by Williams et al. (McGowan, et al., *Tetrahedron Lett.* 38:331, 1997), i.e. the use of $BrCCl_3$ and DBU in dichloromethane, was less efficient (ca. 40%).

We have found that the HPLC retention time (Song, et al., supra, 2002) and spectroscopic properties of the synthesized compound 5 are identical in all respects to those of the endogenous AHR ligand isolated in our laboratory from pig lung. Its successful synthesis, therefore, unequivocally confirms the structure and allows for further biological testing aimed at establishing its physiological role in living organisms.

Example 1

Preparation of (2R)-2-[2'-(1"H-indol-3"-yl)-2'-oxo-acetyloamino]-3-mercaptopropionic acid methyl ester (3). To a stirred suspension of indoleglyoxylyl chloride 1 (2.07 g, 10 mmol) and L-cysteine methyl ester hydrochloride 2 (2.57 g, 15 mmol) in a dry benzene (150 mL) was added dropwise triethylamine (4.2 mL, 3.03 g, 30 mmol) with stirring at 0° C. Cooling bath was removed and the mixture was stirred at room temperature for 20 hours and then refluxed for 2.5 hours. The warm solution was filtered and a precipitate washed with benzene. Filtrate was washed with sat. $NaHCO_3$ and water, dried ($Na_2SO_4$) and evaporated. The crystalline residue was purified by flash chromatography. Elution with chloroform/methanol (99:1) gave pure compound 3 (1.68 g, 55%) that was crystallized from benzene: m.p. 145–146° C.; $[\alpha]^{22}_D$+193° (c 0.8, $CHCl_3$); UV (EtOH) $\lambda_{max}$ 255.5 nm ($\epsilon$ 11,000), 266.0 nm ($\epsilon$ 9,600), 273.5 nm ($\epsilon$ 8,700), 330.5 nm ($\epsilon$ 9,700); IR (KBr) 3358, 3262, 2952, 2941, 2538, 1750, 1744, 1662, 1605, 1500, 1493, 1434, 1352, 1314, 1235, 1227, 1157, 1135, 744 cm$^{-1}$; $^1$H NMR (500 MHz, $CDCl_3$) δ 9.02 (1H, d, J=3.3 Hz, 2"-H), 8.84 (1H, m, N$\underline{H}_{indole}$), 8.44 (1H, m, 4"-H), 8.25 (1H, br d, J=ca. 8 Hz, CON$\underline{H}$), 7.45 (1H, m, 7"-H), 7.35 (2H, br m, 5"- and 6"-H), 4.92 (1H, ~dt, J=8.2, 4.7 Hz, C$\underline{H}CO_2Me$), 3.83 (3H, s, $CO_2Me$), 3.06 and 3.12 (each 1H, each ~ddd, J=14, 9, 4.7 Hz, C$\underline{H}_2SH$), 1.50 (1H, t, J=9.0 Hz, $CH_2SH$); $^1$H NMR (500 MHz, $CD_3OD$) δ 8.77 (1H, s, 2"-H), 8.30 (1H, m, 4"-H), 7.46 (1H, m, 7"-H), 7.25 (2H, m, 5"- and 6"-H), 4.77 (1H, part X of ABX system, J=6.6, 4.8 Hz, C$\underline{H}CO_2Me$), 3.78 (3H, s, $CO_2Me$), 3.08 (1H, part A of ABX system, J=14.1, 4.8 Hz, one of C$\underline{H}_2SH$), 3.01 (1H, part B of ABX system, J=14.1, 6.6 Hz, one of C$\underline{H}_2SH$); $^{13}$C NMR (125 MHz, $CD_3OD$) δ 181.85 (s, $\underline{C}OCONH$), 171.69 (s, $\underline{C}OOMe$), 165.27 (s, CO$\underline{C}ONH$), 139.76 (d, C-2"), 137.98 (s, C-7a"), 127.86 (s, C-3a"), 124.92, 123.93 and 122.99 (each d; C-4", -5" or -6"), 113.96 (s, C-3"), 113.14 (d, C-7"), 55.85 (d, $\underline{C}HCO_2Me$), 53.16 (q, $CO_2\underline{Me}$), 26.48 (t, $CH_2SH$); MS (EI) m/z (relative intensity) no M$^+$, 273 (M$^+$–SH, 0.5), 256 (2), 233 (2), 185 (2), 183 (2), 153 (19), 144 (indole-C(O)—, 22), 136 (8), 115 (8), 107 (25), 91 (100), 77 (63), 59 (51); MS (ESI) m/z 329.0568 (M$^+$+Na), $C_{14}H_{14}N_2O_4SNa$ requires 329.0572; Anal. (calcd for $C_{14}H_{14}N_2O_4S$): C, 54.89; H, 4.61; N, 9.15; S, 10.47. Found: C, 54.87; H, 4.65; N, 9.17; S, 10.40. The compound gave a single peak on HPLC (20% 2-propanol in hexane, 10 mm×25 cm Zorbax-Sil column, 4 mL/min) at $R_V$ 27 mL.

Example 2

Preparation of (4R)-2-(1'H-indole-3'-carbonyl)-4,5-dihydro-thiazole-4-carboxylic acid methyl ester (4). To a stirred solution of indoleglyoxamide 3 (2.53 g, 8.3 mmol) in anhydrous methylene chloride (300 mL) was added $TiCl_4$ (1 M sol. in $CH_2Cl_2$, 8.4 mL, 8.4 mmol) dropwise at room temperature. The mixture was then refluxed for 5 hours, cooled to room temperature, stirred overnight (16 hours) and quenched by an addition of saturated $NaHCO_3$. The organic layer was washed with water, dried ($MgSO_4$) and evaporated. The residue was purified by flash chromatography. Elution with chloroform/methanol (99:1) gave pure compound 4 (0.6 g, 25%) that was crystallized from methanol/benzene: m.p. 190–191° C.; $[\alpha]^{22}_D$+64° (c 0.5, $CHCl_3$); UV (EtOH) $\lambda_{max}$ 261.0 nm ($\epsilon$ 8,900), 268.5 nm ($\epsilon$ 9,200), 275.5 nm ($\epsilon$ 8,800), 333.0 nm ($\epsilon$ 8,200); IR (KBr) 3420, 3222, 2956, 1748, 1604, 1597, 1580, 1514, 1488, 1458, 1432, 1314, 1233, 1212, 1187, 1133, 1071, 1055, 805, 776, 752 cm$^{-1}$; $^1$H NMR (500 MHz, $CD_3COCD_3$) δ 11.27 (1H, m, NH), 8.82 (1H, d, J=3.2 Hz, 2'-H), 8.34 (1H, m, 4'-H), 7.56 (1H, m, 7'-H), 7.27 (2H, m, 5'- and 6'-H), 5.59 (1H, part X of ABX system, ~t, J=ca. 9.5 Hz, 4-H), 3.80 (3H, s, $CO_2Me$), 3.67 (1H, part A of ABX system, J=11.3, 10.1 Hz, one of 5-$H_2$), 3.58 (1H, part B of ABX system, J=11.3, 8.9 Hz, one of 5-$H_2$); $^{13}$C NMR (125 MHz, $CD_3COCD_3$) δ 179.71 (s, C=O), 173.88 (s, C-2), 171.14 (s, $\underline{C}OOMe$), 138.73 (d, C-2'), 137.39 (s, C-7a'), 127.22 (s, C-3a'), 124.31, 123.32 and 122.45 (each d, C-4', -5' or -6'), 114.06 (s, C-3'), 112.92 (d, C-7'), 80.49 (d, C-4), 52.65 (q, $CO_2\underline{Me}$), 33.62 (t, C-5); MS (EI) m/z (relative intensity) 288 (M$^+$, 29), 256 (M$^+$–MeOH, 4), 236 (7), 229 (M$^+$–$CO_2Me$, 6), 202 (4), 144 (100), 137 (15), 116 (M$^+$–$C_6H_6O_3SN$, 15), 95 (16), 81 (41), 69 (87); MS (ESI) m/z 311.0454 (M$^+$+Na), $C_{14}H_{12}N_2O_3SNa$ requires 311.0466; Anal. (calcd for $C_{14}H_{12}N_2O_3S$): C, 58.32; H, 4.20; N, 9.72; S, 11.12. Found: C, 58.34; H, 4.09; N, 9.77; S, 10.82. The compound gave a single peak on HPLC (20% 2-propanol in hexane, 10 mm×25 cm Zorbax-Sil column, 4 mL/min) at $R_V$ 39 mL.

Example 3

Preparation of 2-(1'H-indole-3'-carbonyl)-thiazole-4-carboxylic acid methyl ester (5). (a) Freshly activated manganese (IV) oxide (115 mg, 1.3 mmol) was added to a solution of indole-thiazoline ketone 4 (38 mg, 0.13 mmol) in anhydrous methylene chloride (30 mL). The resulting suspension was stirred for 3 hours at room temperature and then concentrated. The residue was purified by column chromatography. Elution with chloroform/methanol (99:1) gave pure compound 5 (33 mg, 88%) that was crystallized from methanol: m.p. 234–235° C.; UV (EtOH) $\lambda_{max}$ 271.0 nm ($\epsilon$ 10,500), 278.0 nm ($\epsilon$ 11,400), 356.5 nm ($\epsilon$ 11,700); IR (KBr) 3452, 3241, 3125, 2957, 2927, 1737, 1593, 1577, 1507, 1482, 1466, 1432, 1338, 1234, 1206, 1202, 1128, 1113, 1102, 1063, 816, 782, 776, 755, 642 cm$^{-1}$; $^1$H NMR MHz, CD$_3$COCD$_3$) δ 11.33 (1H, m, NH), 9.30 (1H, s, 2'-H), 8.70 (1H, s, 5-H), 8.44 (1H, m, 4'-H), 7.61 (1H, m, 7'-H), 7.30 (2H, m, 5'- and 6'-H), 3.94 (3H, s, CO$_2$Me); $^1$H NMR (500 MHz, CD$_3$OD) δ 9.25 (1H, s, 2'-H), 8.66 (1H, s, 5-H), 8.36 (1H, m, 4'-H), 7.51 (1H, m, 7'-H), 7.28 (2H, m, 5'- and 6'-H), 3.99 (3H, s, CO$_2$Me); $^1$H NMR (500 MHz, DMSO-d$_6$) δ 9.08 (1H, s, 2'-H), 8.86 (1H, m, 5-H), 8.30 (1H, m, 4'-H), 7.59 (1H, m, 7'-H), 7.28 (2H, m, 5'- and 6'-H), 3.91 (3H, s, CO$_2$Me); $^{13}$C NMR (125 MHz, DMSO-d$_6$) δ 176.45 (s, C=O), 169.86 (s, C-2), 161.01 (s, CO$_2$Me), 146.89 (s, C-4), 137.98 (d, C-2'), 136.34 (s, C-7a'), 133.90 (d, C-5), 126.35 (s, C-3a'), 123.63, 122.70 and 121.40 (d, C-4', -5' or -6'), 112.72 (d, C-7'), 112.04 (s, C-3'), 52.35 (q, CO$_2$Me); MS (EI) m/z (relative intensity) 286 (M$^+$, 70), 144 (M$^+$−C$_5$H$_4$O$_2$SN, 100), 116 (M$^+$−C$_6$H$_4$O$_3$SN, 17), 89 (14), 69 (18); MS (ESI) m/z 309.0297 (M$^+$+Na), C$_{14}$H$_{10}$N$_2$O$_3$SNa requires 309.0310. Anal. (calcd for C$_{14}$H$_{10}$N$_2$O$_3$S): C, 58.73; H, 3.52; N, 9.78; S, 11.20. Found: C, 58.83; H, 3.46; N, 9.94; S, 11.12.

(b) Nickel peroxide (assay ~30% active NiO$_2$) (120 mg, 1.3 mmol) was added to a solution of indole—thiazoline ketone 4 (38 mg, 0.13 mmol) in anhydrous methylene chloride (30 mL). The resulting suspension was stirred for 19 hours at room temperature and then concentrated. The residue was purified by column chromatography. Elution with chloroform/methanol (99:1) gave pure product 5 (28 mg, 75%) that was crystallized from methanol. The spectroscopic properties of the synthesized compound were identical in all respects with those described in EXAMPLE 3a.

(c) To a stirred suspension of indole—thiazoline ketone 4 (255 mg, 0.88 mmol) in methylene chloride (30 mL) was added dropwise DBU (148 mg, 146 μL, 0.98 mmol) at 0° C. The solution turned red and became clear. Then bromotrichloromethane (178 mg, 88 μL, 0.90 mmol) was added dropwise. The yellow solution was stirred for 4.5 hours at 0° C. and for 20 hours in cold room (ca. 6° C.). Saturated NH$_4$Cl was added and phases separated. Organic layer was washed with water, dried (MgSO$_4$), and evaporated. The residue was redissolved in chloroform, applied on a silica Sep-Pak (5 g) and eluted with 1% MeOH in chloroform. The corresponding fractions containing indole-thiazole-ketone 5 were combined, evaporated and the residue (156 mg) was subjected to HPLC (10% 2-propanol in hexane, 10 mm×25 cm Zorbax Silica column, 4 mL/min) separation. The product 5 collected at R$_V$ 42 mL (104 mg, 40%). The spectroscopic properties of the synthesized compound were identical in all respects with those described in EXAMPLE 3a.

What is claimed is:

1. A compound of the formula II

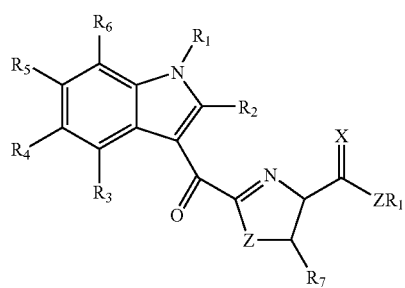

wherein: R1 maybe hydrogen or can be selected from the group consisting of (C1–C6)-alkyl and (C3–C7)-cycloalkyl, and wherein the alkyl group can be substituted by (C3–C7)-cycloalkyl or can be mono- or polysubstituted by an aryl group, wherein the aryl group can be mono- or polysubstituted by halogen, (C1–C6)-alkyl, (C3–C7)-cycloalkyl, hydroxy and nitro groups;

R1 may be an aryl, wherein the aryl group can be mono- or polysubstituted by halogen, (C1–C6)-alkyl, (C3–C7)-cycloalkyl, hydroxy and nitro groups;

R1 may further be a protecting group;

R2, R3, R4, R5, R6, and R7 may be the same or different and are each selected from the group consisting of hydrogen, (C1–C6)-alkyl, (C3–C7)-cycloalkyl, (C1–C6)-acyl, (C1–C6)-alkoxy, alkoxycarbonyl (COOR1) halogen, benzyloxy, the nitro group, the amino group, the (C1-C4)-mono or dialkyl-substituted amino group, or an aryl group, wherein the aryl group can be mono- or polysubstituted by halogen, (C1–C6)-alkyl, (C3–C7)-cycloalkyl, hydroxy and nitro groups;

X and Z may be the same or different and are each selected from the group consisting of O, S and NH; and wherein the stereochemical centers, i,e., the carbons bearing C(X)ZR1 and R7 substituent may have R or S configuration.

2. A compound of the formula XI

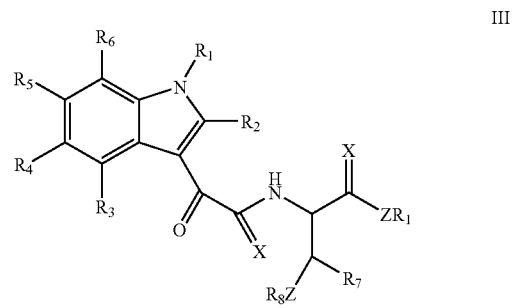

wherein: R1 may be hydrogen or can be selected from the group consisting of (C1–C6)-alkyl and (C3–C7)-cycloalkyl, and wherein the alkyl group can be substituted by (C3–C7)-cycloalkyl or can be mono- or polysubstituted by an aryl group, wherein the aryl group can be mono- or polysubstituted by halogen, (C1–C6)-alkyl, (C3–C7)-cycloalkyl, hydroxy and nitro groups;

R1 may be an aryl group, wherein the aryl group can be mono- or polysubstituted by halogen, (C1–C6)-alkyl, (C3–C7)-cycloalkyl, hydroxy and nitro groups;

R1 may further be a protecting group;

R2, R3, R4, R5, R6, and R7 may be the same or different and are each selected from the group consisting of hydrogen, (C1–C6)-alkyl, (C3–C7)-cycloalkyl, (C1–C6)-acyl, (C1–C6)-alkoxy, alkoxycarbonyl (COOR1), halogen, benzyloxy, the nitro group, the amino group, the (C1–C4)-mono or dialkyl-substituted amino group, or an aryl group, wherein the aryl group, can be mono- or polysubstituted by halogen, (C1–C6)-alkyl, (C3–C7)-cycloalkyl, hydroxy and nitro groups;

X and Z may be the same or different and are each selected from the group consisting of O, S and NH; and wherein all the stereochemical centers of the tetrahydro-1,3-azole fragment may have R or S configuration.

* * * * *

UNITED STATES PATENT AND TRADEMARK OFFICE
CERTIFICATE OF CORRECTION

PATENT NO. : 7,241,900 B2  Page 1 of 1
APPLICATION NO. : 11/286537
DATED : July 10, 2007
INVENTOR(S) : Hector F. DeLuca, Pawel K. Grzywacz and Rafal R. Sicinski It is certified that error appears in the above-identified patent and that said Letters Patent is hereby corrected as shown below:

Col. 2, Line 15 "HHIF-1a/" should be -- HIF-1alpha/ --

Col. 6, Line 54 "formula VIII" should be -- formula VII --

Col. 19, Line 66, Claim 1 "R1 maybe" should be -- R1 may be --

Col. 20, Line 6, Claim 1 "an aryl, wherein" should be -- an aryl group, wherein --

Signed and Sealed this

First Day of April, 2008

JON W. DUDAS
*Director of the United States Patent and Trademark Office*